US00PP18396P2

(12) United States Plant Patent

Head et al.

(10) Patent No.: US PP18,396 P2
(45) Date of Patent: Jan. 1, 2008

(54) *LEUCOTHOE* PLANT NAMED 'HOWW'

(50) Latin Name: *Leucothoe fontanesiana*
Varietal Denomination: HOWW

(75) Inventors: William A. Head, Walhalla, SC (US); Robert H. Head, Seneca, SC (US); Lisa Jones Head, Seneca, SC (US)

(73) Assignee: Head Ornamentals, Inc., Seneca, SC (US)

( * ) Notice: Subject to any disclaimer, the term of this patent is extended or adjusted under 35 U.S.C. 154(b) by 0 days.

(21) Appl. No.: 11/513,612

(22) Filed: Aug. 31, 2006

(51) Int. Cl.
*A01H 5/00* (2006.01)

(52) U.S. Cl. ..... Plt./226

(58) Field of Classification Search ..... Plt./226
See application file for complete search history.

*Primary Examiner*—Kent Bell
*Assistant Examiner*—S. B. McCormick-Ewoldt
(74) *Attorney, Agent, or Firm*—C. A. Whealy

(57) ABSTRACT

A new and distinct cultivar of *Leucothoe* plant named 'HOWW', characterized by its deliquescent mounding fountain-like shrub; vigorous growth habit; fully expanded leaves are green and greyed-green mottled with distinct ivory white-colored margins; developing leaves with reddish overtones; freely flowering plant habit; white-colored flowers arranged in long racemes, good garden performance; and relative resistance to *Phytophthora* root rot.

3 Drawing Sheets

Botanical description: *Leucothoe fontanesiana.*
Cultivar denomination: 'HOWW'.

BACKGROUND OF THE INVENTION

The present invention relates to a new and distinct cultivar of *Leucothoe,* botanically known as *Leucothoe fontanesiana* and hereinafter referred to by the name 'HOWW'.

The new *Leucothoe* is a product of a planned breeding program conducted by the Inventors in Seneca, S.C. The objective of the breeding program is to create new *Leucothoe* cultivars with desirable plant form, plant size and leaf coloration.

The new *Leucothoe* originated from a self-pollination made by the Inventors in May, 1988, in Seneca, S.C. of an unnamed selection of *Leucothoe fontanesiana,* not patented. The new *Leucothoe* was discovered and selected by the Inventor as a single flowering plant within the progeny of the stated self-pollination in a controlled environment in Seneca, S.C. in March, 1989.

Asexual reproduction of the new *Leucothoe* by terminal cuttings in a controlled environment in Seneca, S.C. since October, 1991, has shown that the unique features of this new *Leucothoe* are stable and reproduced true to type in successive generations.

SUMMARY OF THE INVENTION

The cultivar HOWW has not been observed under all possible environmental conditions. The phenotype may vary somewhat with variations in environment and cultural practices such as temperature, daylength and light intensity without, however, any variance in genotype.

The following traits have been repeatedly observed and are determined to be the unique characteristics of 'HOWW'. These characteristics in combination distinguish 'HOWW' as a new and distinct cultivar of *Leucothoe:*

1. Deliquescent mounding fountain-like shrub; vigorous growth habit.
2. Fully expanded leaves are green and greyed-green mottled with distinct ivory white-colored margins; developing leaves with reddish overtones.
3. Freely flowering plant habit.
4. White-colored flowers arranged in long racemes.
5. Good garden performance.
6. Relatively resistant to *Phytophthora* root rot.

Plants of the new *Leucothoe* can be compared to plants of the parent selection. Plants of the new *Leucothoe* differ primarily from plants of the parent selection in leaf coloration as plants of the new *Leucothoe* have green and greyed-green mottled leaves with distinct ivory white-colored margins whereas plants of the parent selection have green-colored leaves. In addition, leaves of plants of the new *Leucothoe* are shorter than leaves of plants of the parent selection.

Plants of the new *Leucothoe* can be compared to plants of the cultivar Tricolor, disclosed in U.S. Plant Pat. No. 11,008. In side-by-side comparisons conducted in Seneca, S.C., plants of the new *Leucothoe* differed from plants of the cultivar Tricolor in the following characteristics:

1. Plants of the new *Leucothoe* were more vigorous and hardier than plants of the cultivar Tricolor.
2. Plants of the *Leucothoe* and the cultivar Tricolor differed in leaf coloration as leaves of plants of the cultivar Tricolor were red, green and yellow in color.
3. Plants of the new *Leucothoe* were more freely flowering than plants of the cultivar Tricolor.

Plants of the new *Leucothoe* can be compared to plants of the cultivar Girard's Rainbow, not patented. In side-by-side comparisons conducted in Seneca, S.C., plants of the new *Leucothoe* differed from plants of the cultivar Girard's Rainbow in the following characteristics:

1. Plants of the new *Leucothoe* were larger, more vigorous and hardier than plants of the cultivar Girard's Rainbow.

2. Plants of the new *Leucothoe* and the cultivar Girard's Rainbow differed in leaf coloration as leaves of plants of the cultivar Girard's Rainbow were green and yellow mottled in color.
3. Plants of the new *Leucothoe* were more freely flowering than plants of the cultivar Girard's Rainbow.
4. Plants of the new *Leucothoe* were more resistant and tolerant to pathogens common to *Leucothoe* than plants of the cultivar Girard's Rainbow.

BRIEF DESCRIPTION OF THE PHOTOGRAPHS

The accompanying colored photographs illustrate the overall appearance of the new *Leucothoe,* showing the colors as true as it is reasonably possible to obtain in colored, reproductions of this type. Colors in the photographs may differ slightly from the color values cited in the detailed botanical description which accurately describe the colors of the new *Leucothoe.*

The photograph on the first sheet comprises a side perspective view of a typical flowering plant of 'HOWW' grown in container.

The photograph on the second sheet comprises a side perspective view of a typical flowering plant of 'HOWW' with developing foliage.

The photograph on the third sheet comprises a close-up view of typical inflorescences and leaves of 'HOWW'.

DETAILED BOTANICAL DESCRIPTION

The photographs and following observations, measurements and values describe plants grown in Seneca, S.C., under commercial practice in a polypropylene-covered shadehouse in three-gallon containers. During the production of the plants, day temperatures ranging from −5° C. to 40° C. and night temperatures ranging from −25° C. to 35° C. Plants had been growing for about four years when the photographs and description were taken. In the following description, color references are made to The Royal Horticultural Society Colour Chart, 2001 Edition, except where general terms of ordinary dictionary significance are used.

Botanical classification: *Leucothoe fontanesiana* cultivar HOWW.

Parentage: Self-pollination of an unnamed selection of *Leucothoe fontanesiana,* not patented.

Propagation:

*Type.*—By semi-hardwood and hardwood stem cuttings.

*Time to initiate roots, summer.*—About 45 days at temperatures of 27° C. to 30° C.

*Time to initiate roots, winter.*—About 70 days at temperatures of 16° C. to 17° C.

*Time to produce a rooted young plant, summer.*—About 80 days at temperatures of 27° C. to 30° C.

*Time to produce a rooted young plant, winter.*—About 120 days at temperatures of 16° C. to 17° C.

*Root description.*—Fine, fibrous; 159B to N167D in color.

*Rooting habit.*—Freely branching; dense.

Plant description:

*Plant and growth habit.*—Deliquescent mounding fountain-like shrub. Vigorous growth habit.

*Branching habit.*—Clumping with numerous basal branches and about seven lateral branches

*Plant height.*—About 90 cm to 120 cm.

*Plant diameter.*—About 120 cm to 150 cm.

Lateral branch description:

*Length.*—About 8 cm to 36 cm.

*Diameter.*—About 1.9 mm to 5.2 mm.

*Internode length.*—About 1.1 cm to 3.1 cm.

*Strength.*—Strong; flexible.

*Texture.*—Smooth, glabrous.

*Color.*—Young stems, upper surface: 183A. Young stems, lower surface: 191A. Older stems: 165B.

Foliage description:

*Arrangement.*—Alternate; simple.

*Length.*—About 2.5 cm to 10 cm.

*Width.*—About 0.6 cm to 2.5 cm.

*Shape.*—*Lanceolate.*

*Apex.*—Long acuminate.

*Base.*—Broadly cuneate.

*Margin.*—Serrate; coarse.

*Texture, upper surface.*—Scattered pubescent.

*Texture, lower surface.*—Pubescent.

*Venation pattern.*—Pinnate.

*Color.*—Developing foliage, upper surface: Center, 137A, overlain with 183A; towards the margins, 155A overlain with 65B. Developing foliage, lower surface: Center, 182D; towards the margins, 65D. Fully expanded foliage, upper surface: Center, 139A mottled with 191B; towards the margin, 155A; venation, 137A. Fully expanded foliage, lower surface: Center, 191A; towards the margins, 155A; venation, 145C.

*Petiole.*—Length: About 5.6 mm to 14.6 mm. Diameter: About 1.4 mm to 2.8 mm. Texture, upper and lower surfaces: Minutely hirsute. Color, upper surface: 183A. Color, lower surface: 191A.

Flower description:

*Flower arrangement and habit.*—Urceolate flowers arranged in long axillary racemes. Freely flowering habit with usually about 20 to 50 open flowers per inflorescence. Flowers not persistent. Flowers downwardly drooping.

*Fragrance.*—Faint; musky.

*Natural flowering season.*—Plants of the new *Leucothoe* flower from during the early spring in South Carolina.

*Flower longevity.*—Individual flowers last about one to three days on the plant.

*Inflorescence height.*—About 2 cm to 6.5 cm.

*Inflorescence diameter.*—About 1.5 cm to 1.7 cm.

*Flower diameter.*—About 3.5 mm to 5.1 mm.

*Flower length* (*height*).—About 5 mm to 8.5 mm.

*Flower bud.*—Shape: Ovate to oblong. Length: About 3.2 mm to 7.5 mm. Diameter: About 2 mm to 4.5 mm. Color: 157C.

*Corolla.*—Arrangement: Five petals fused at the base; ovate to oblong urceolate corolla tube. Petal length from throat: About 1 mm. Peal width: About 1.5 mm. Petal shape: Orbicular to elliptic. Petal apex: Rounded. Petal margin: Entire. Petal texture, upper and lower surfaces: Smooth, waxy. Color: Petal, when opening, upper and lower surfaces: 157C. Petal, fully opened, upper and lower surfaces: 157D; color becoming closer to 155D with development.

*Calyx.*—Arrangement: Calyx tube with five sepals fused at the base. Sepal length: About 2 mm. Sepal width: About 1 mm. Sepal shape: Oblong to ovate. Sepal apex: Acute. Sepal margin: Entire. Sepal texture, upper and lower surfaces: Smooth; waxy. Color, upper and lower surfaces: 157C.

*Peduncles.*—Length: About 2.5 cm to 8.5 cm. Diameter: About 0.8 mm to 2.5 mm. Angle: About 45° to 90° from stem axis. Strength: Strong; flexible. Texture; Smooth, glabrous. Color: 157C.

*Pedicels.*—Length: About 1.2 mm to 4 mm. Diameter: About 0.6 mm. Angle: About 45° to 90° from peduncle axis. Strength: Strong; flexible. Texture: Smooth, glabrous. Color: 157C.

*Reproductive organs.*—Stamens: Quantity/arrangement: Ten per flower. Anther shape: Oblong. Anther length: About 0.5 mm to 1 mm. Anther color: 157C. Pollen amount: Scarce. Pollen color: 157C. Pistils: Quantity: One per flower. Pistil length: About 4 mm to 7 mm. Style length: About 3 mm to 4 mm. Style color: 157C. Stigma shape: Flared, blunt. Stigma color: 157C. Ovary color: 157C. Fruit: Quantity per plant: Fifty to 500 per lateral branch. Length: About 2 mm to 3 mm. Diameter: About 2 mm to 3 mm. Texture: Smooth. Color: 165A. Seed: Length: About 0.3 mm. Diameter: About 0.1 mm. Color: 164D.

Garden performance: Plants of the new *Echinacea* have exhibited good tolerance to rain and wind and have been observed to tolerant temperatures from about −25° C. to about 45° C.

Pathogen/pest resistance: Plants of the new *Leucothoe* have been observed to be resistant to *Phytophthora* root rot and tolerant to *Cercospora* leaf spot. Plants of the new *Leucothoe* have not been observed to be resistant to pests and other pathogens common to *Leucothoe*.

It is claimed:

1. A new and distinct *Leucothoe* plant named 'HOWW' as illustrated and described.

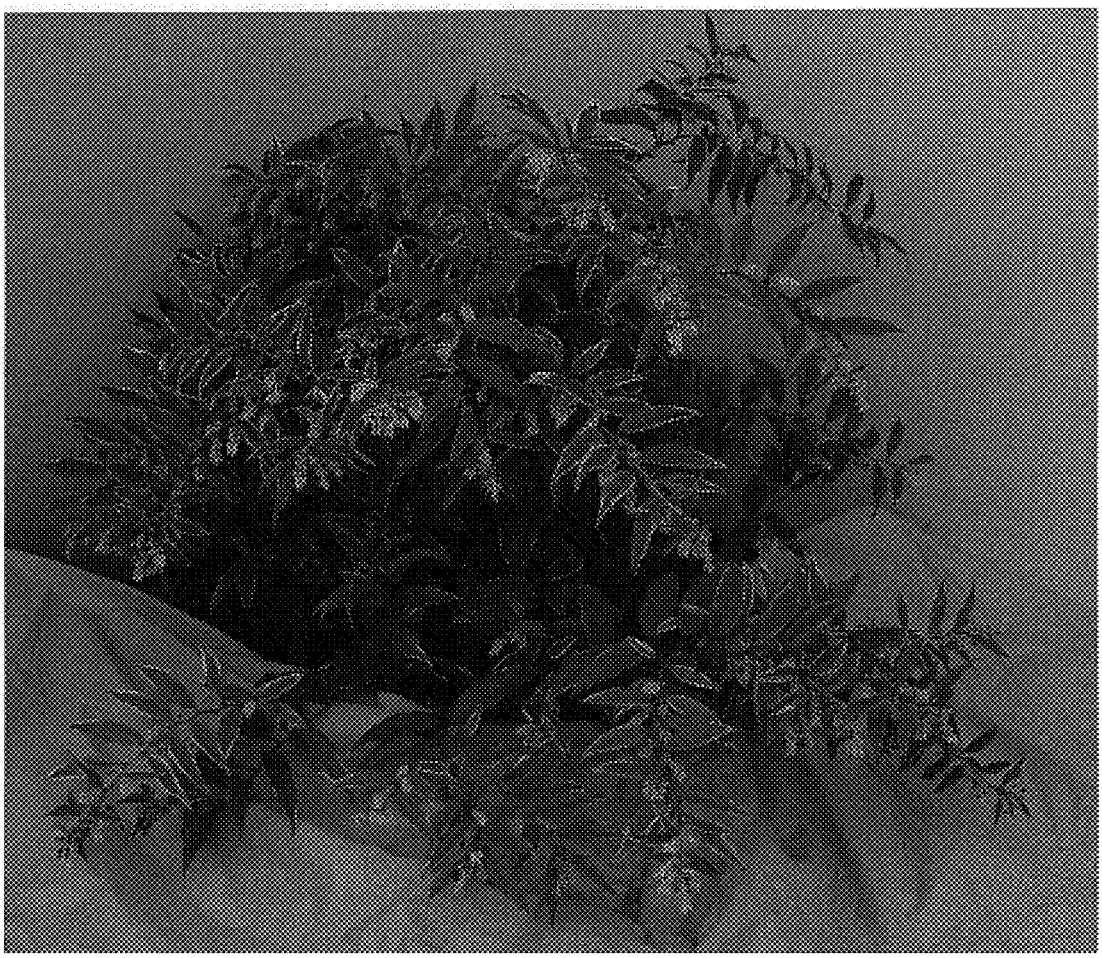

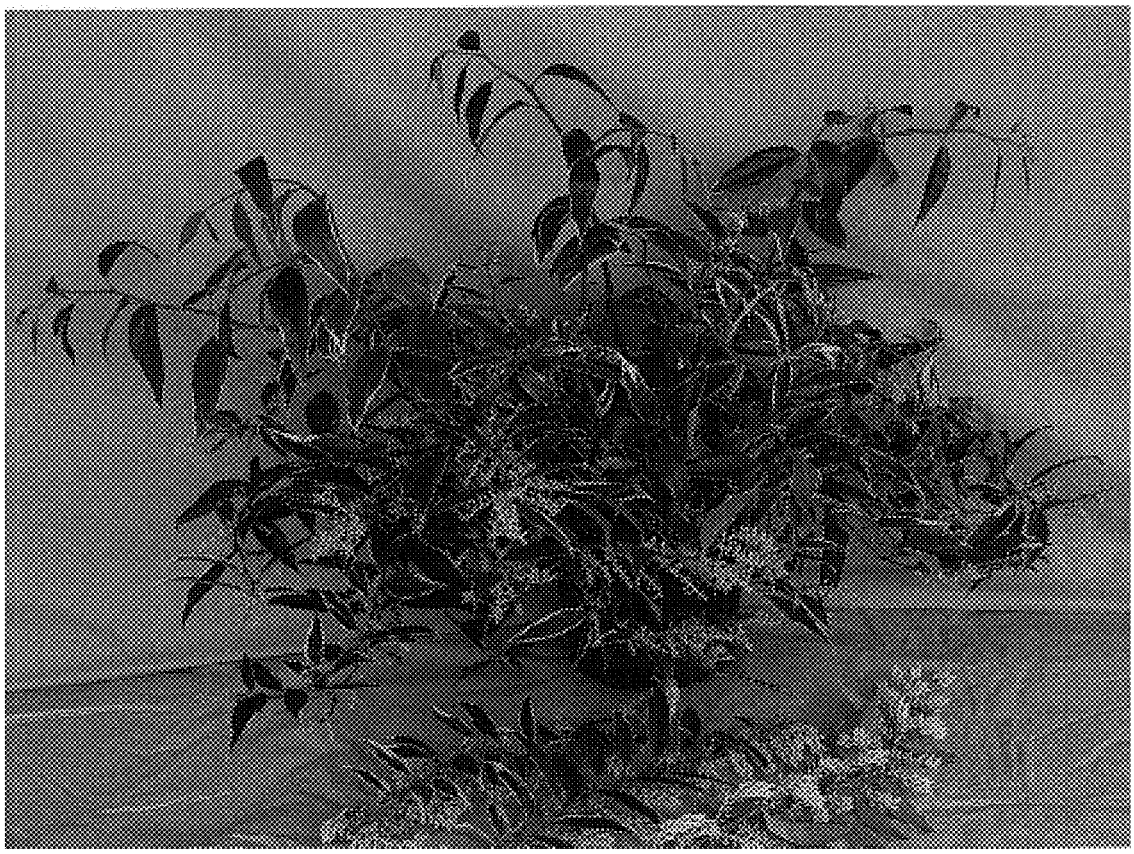

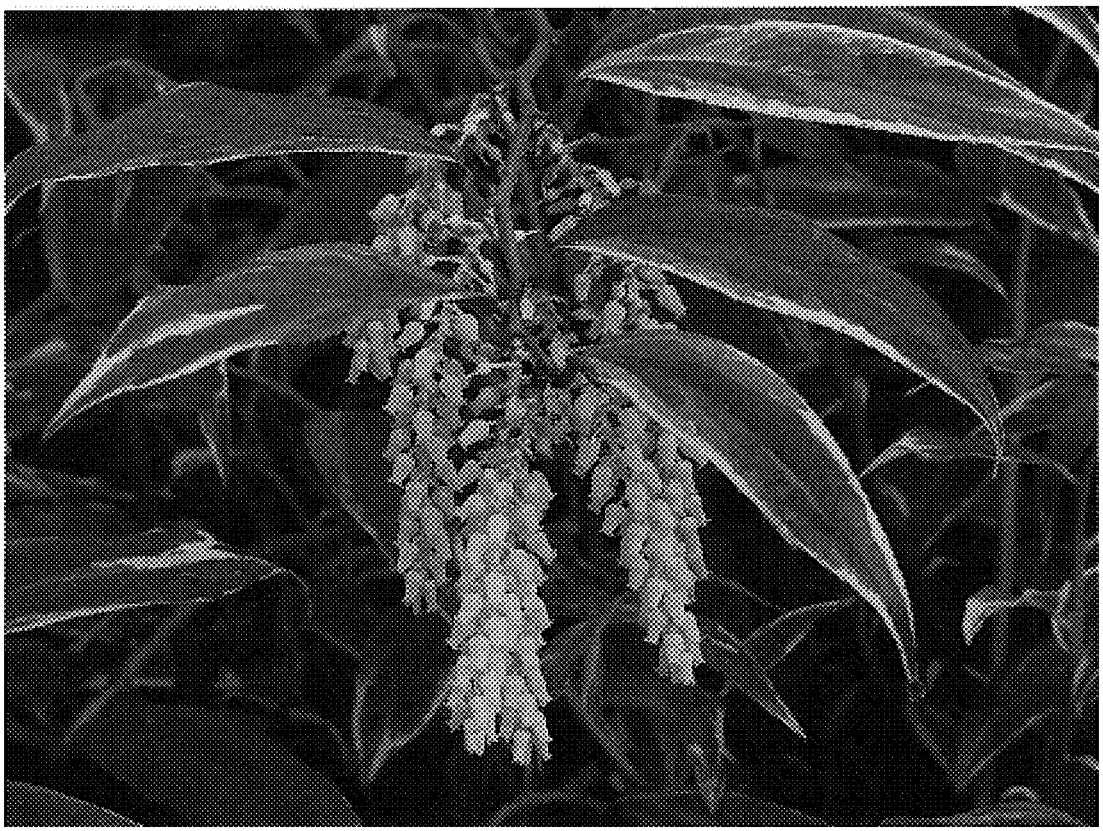

* * * * *